(12) United States Patent
Warren et al.

(10) Patent No.: US 9,546,403 B1
(45) Date of Patent: Jan. 17, 2017

(54) SUBSTRATE FOR METHYLATED DNA TESTING

(71) Applicant: University of Utah Research Foundation, Salt Lake City, UT (US)

(72) Inventors: Jorja DeGrado Warren, Ogden, UT (US); Wei Xiong, Draper, UT (US); Karen A. Heichman, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 149 days.

(21) Appl. No.: 13/715,950

(22) Filed: Dec. 14, 2012

Related U.S. Application Data

(60) Provisional application No. 61/630,554, filed on Dec. 14, 2011.

(51) Int. Cl.
   *C12Q 1/68* (2006.01)

(52) U.S. Cl.
   CPC ........... *C12Q 1/6886* (2013.01); *C12Q 1/6883* (2013.01)

(58) Field of Classification Search
   None
   See application file for complete search history.

(56) References Cited

U.S. PATENT DOCUMENTS

| | | | |
|---|---|---|---|
| 7,749,702 | B2 | 7/2010 | Lofton-Day et al. |
| 2007/0224626 | A1* | 9/2007 | Jeddeloh ............. C12Q 1/6886 435/6.12 |
| 2008/0081333 | A1* | 4/2008 | Mori et al. ......... 435/6 |
| 2008/0193931 | A1* | 8/2008 | Li .......... C12Q 1/6816 435/6.18 |
| 2009/0305256 | A1* | 12/2009 | Pfeifer ............. C12Q 1/6886 435/6.12 |

FOREIGN PATENT DOCUMENTS

| | | | |
|---|---|---|---|
| WO | WO2007132166 | * | 11/2007 |
| WO | WO2009115920 | * | 9/2009 |

OTHER PUBLICATIONS

Warren, et al.; "Septin 9 methylated DNA is a sensitive and specific blood test for colorectal cancer"; BMC Medicine; 2011; 9 pages; vol. 133.

Xue, et al.; "Optimizing the yield and utility of circulating cell-free DNA from plasma and serum"; Clinica Chimica Acta; 404 (2009) 100-104.

\* cited by examiner

*Primary Examiner* — James Martinell
(74) *Attorney, Agent, or Firm* — Thorpe North & Western, LLP

(57) ABSTRACT

Methods, kits and compositions drawn related to providing controls in diagnostic testing are provided. In one embodiment, a method of verifying proper function of a test for detecting and/or classifying a disease or disorder for which manifestation of a methylated gene is a biomarker is provided. The method includes performing a test for detecting, monitoring, or classifying a disease or disorder, or predisposition thereto, for which manifestation of a methylated gene is a biomarker and verifying proper function of the test by performing (e.g. duplicating or repeating) the test utilizing a control that originates from at least one pregnant female animal. The test includes determining the methylation status of at least one biomarker from a biological sample obtained from an animal subject and verifying proper function of the test by performing the test utilizing a control that originates from at least one pregnant female animal.

10 Claims, No Drawings

SUBSTRATE FOR METHYLATED DNA TESTING

PRIORITY DATA

This application claims the benefit of U.S. Provisional Patent Application Ser. No. 61/630,554, filed Dec. 14, 2011, which is incorporated herein by reference.

FIELD OF THE INVENTION

The present invention relates to DNA sequences that exhibit altered methylation patterns in certain states, including diseased or otherwise altered states, relative to normal. Particular embodiments provide for novel methods, kits, and compositions that can be used as controls or for testing verification. In certain embodiments, such testing may be in conjunction with detection methods for certain diseases or disorders that manifest through elevated levels of methylation in certain genes or other DNA sequences.

BACKGROUND OF THE INVENTION

A variety of cancers and other disorders have been associated with increased methylation of certain genes. For example, Septin 9 (SEPT9 gene) methylated DNA has been demonstrated to appear in the blood plasma of individuals with colorectal cancer and adenomatous polyps. There have been several SEPT9 methylated DNA assays developed to screen for colorectal cancer. Typically, assays or tests for the presence of methylated genes rely on controls using synthesized completely methylated genomic DNA from cell line sources. However, it is desirable to find a new source of methylated DNA that better represents the state of naturally occurring methylated DNA and can function as a control.

SUMMARY OF THE INVENTION

In accordance with the purpose(s) of this invention, as embodied and broadly described herein, the present invention, in one aspect, is drawn to methods, kits and compositions related to providing controls in research and/or diagnostic testing. In one embodiment, a method of verifying the proper function of an assay or test for analyzing the methylation status of a gene or other DNA sequence is provided. The method includes utilizing a control that originates from at least one pregnant female animal.

In another embodiment, a method of verifying proper function of a test for detecting and/or classifying a disease or disorder for which manifestation of a methylated gene is a biomarker is provided. The method includes performing a test for detecting, monitoring, or classifying a disease or disorder, or predisposition thereto, for which manifestation of a methylated gene is a biomarker and verifying proper function of the test by performing (e.g. duplicating or repeating) the test utilizing a control that originates from at least one pregnant female animal. The test includes determining the methylation status of at least one biomarker from a biological sample obtained from an animal subject and verifying proper function of the test by performing the test utilizing a control that originates from at least one pregnant female animal.

In another embodiment, the present invention provides a method of making a control for use in testing for a disease or disorder or predisposition thereto, wherein a methylated DNA sequence is a biomarker for the disease or disorder or predisposition thereto. The method includes obtaining blood from one or more pregnant female animals, isolating a plasma fraction from the blood, extracting DNA from the plasma fraction, treating the DNA with a reagent or a group of reagents that provides for the determination of the methylation status of said biomarker, and determining the methylation status of the biomarker.

Additionally included in the present invention, is a method of detecting, monitoring or classifying a disease or disorder or predisposition thereto for which manifestation of a methylated gene is a biomarker. Such a method generally includes the steps of performing sample testing, confirming proper functioning of the testing by performing the test utilizing the control made by the methods set forth herein, assessing the methylation status of at least one biomarker, and following confirmation of proper function of the test, assigning a diagnosis or prognosis to the animal subject based on the methylation status of the at least one biomarker gene. Sample testing generally includes the steps of identifying a disease, disorder, or predisposition thereto for which manifestation of a methylated gene is a biomarker and selecting at least one corresponding biomarker gene, collecting a biological sample containing DNA from an animal subject, extracting DNA present in the biological sample, treating the DNA with a reagent or group of reagents that provides for the determination of methylation status of the biomarker, and assessing the methylation status of at least one biomarker in the DNA from the biological sample.

A kit for use in testing for cancers having methylated DNA sequences as biomarkers is also provided by the present invention. In one embodiment, such a kit can include a control containing methylated circulating DNA originating from at least one pregnant female animal and any or all of the following: one or more reagents for extracting DNA, one or more reagents for chemically treating extracted DNA to change the nucleotide sequence of unmethylated DNA sequences, one or more reagents for affinity purifying untreated methylated DNA, one or more reagents for purifying chemically treated DNA, or one or more oligonucleotides with functional properties of either a primer capable of amplifying or sequencing a methylated DNA sequence biomarker which is a biomarker for at least one cancer, or a probe capable of detecting a methylated DNA sequence biomarker. An additional kit is provided for use in the detection or quantification of a target nucleic acid in a biological sample that includes a biological sample from a test subject and a control blood sample from at least one pregnant female animal.

Another kit is provided by the present invention that is for the detection or quantification of a target nucleic acid in a biological sample. In one embodiment, the target nucleic acid can include a methylated gene or a portion of a gene originating from the blood of a pregnant female animal. The biological sample can originate from a test subject known to have, or suspected of having a disease, disorder, or condition for which the target nucleic acid is a biomarker. One example is a neoplasm. In one aspect, the target nucleic acid comprises a methylated gene or a portion of a gene originating from the blood of a pregnant female animal and the biological sample can originate from a test subject known to have, or suspected of having, a disorder such as Angelman syndrome, Prader-Willi syndrome, Lynch syndrome, Beckwith-Wiedemann syndrome or Silver-Russell syndrome.

The present invention also provides an assembly used for the detection or quantification or a target nucleic acid in a biological sample. The assembly, prior to detection or quantification, can include a biological sample from a test subject known to have, or suspected of having, a condition for which the target nucleic acid is known to be a biomarker and a control blood sample from at least one pregnant female animal know to contain the target nucleic acid. The target nucleic acid is typically a gene or a portion of a gene having methylated DNA.

In addition to the above-described methods and kits, compositions for use as controls for detecting, monitoring and/or classifying diseases, disorders, or predispositions thereto, for which methylated DNA is a biomarker, are also set forth. In one embodiment, the control composition can include a diluent and methylated circulating DNA originating from a pregnant animal, wherein the methylated circulating DNA is present in the diluent at a concentration of about 1 pg/mL to about 1000 pg/mL. In another embodiment, the composition can include a diluent and methylated circulating DNA that has undergone chemical treatment to change the nucleotide sequence of unmethylated DNA sequences, wherein the circulating DNA is present in the diluent at a concentration of about 1 pg/mL to about 1000 pg/mL. In another embodiment, the composition can include a diluent and methylated circulating DNA that has been isolated from a blood sample from at least one pregnant female animal utilizing one or more reagents for affinity purification and wherein the methylated circulating DNA is present at a concentration of about 1 pg/mL to about 1000 pg/mL.

DETAILED DESCRIPTION OF THE INVENTION

The invention may be understood more readily by reference to the following detailed description of particular embodiments of the invention.

Particular advantages of the invention will be set forth in part in the description which follows, and in part will be obvious from the description, or may be learned by practice of the invention. The advantages of the invention will be realized and attained by use of the elements and combinations particularly pointed out in the appended claims. It is to be understood that both the foregoing general description and the following detailed description are exemplary and explanatory only and are not restrictive of the invention, as claimed.

Before the present methods, kits, and compositions are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

For the purposes of this disclosure, the term "a" or "an" entity refers to one or more of that entity; for example, "a protein" refers to one or more proteins or at least one protein. As such, the terms "a" or "an", "one or more" and "at least one" can be used interchangeably herein. It is also to be noted that the terms "comprising," "including," and "having" can be used interchangeably. Furthermore, an element or means "selected from the group consisting of" or "comprising one or more of" refers to one or more of the elements in the list that follows, including mixtures (i.e. combinations) of two or more of the elements.

As used herein, the terms "gene" and "DNA sequence" refer to a region of a genomic sequence including all transcript variants, promoter and regulatory elements, and non-coding regions thereof.

As used herein, the term "diluent" refers to a medium of natural or artificial origin that is capable of carrying nucleic acid sequences. Such medium can be liquid, solid, semi-solid, or particulate. For example, in one embodiment, the diluent can be plasma.

As used herein, the term "assay" refers to any procedure for assessing the presence, amount, status or physical state of an analyte or multiple analytes. For example, in one embodiment, the analyte may be nucleic acid.

For the purposes of the invention, numerical or other ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Concentrations, amounts, levels, solubility, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Reference will now be made in detail to particular embodiments of the invention. The present inventors have discovered that pregnant female animals, e.g. pregnant human females, have high concentrations of certain methylated genes which are biomarkers for a number of diseases or disorders. While these pregnant women are generally healthy, the presence of the elevated concentrations of these methylated biomarkers has been found to be highly functional as a control for use in DNA methylation research, diagnostic testing, and monitoring or classifying subjects for diseases or disorders that manifest with elevated methylation levels of certain DNA biomarkers.

Accordingly, a method of verifying the proper function of an assay or test for analyzing the methylation status of a gene or other DNA sequence is provided. The method includes utilizing a control that originates from at least one pregnant female animal. In one aspect, the analyzing of the methylation status of the gene or other DNA sequence can involve detecting the presence or absence of methylation. In another aspect, the analysis of the methylation status of the gene or other DNA sequence can include measuring a level of methylation in the gene or DNA sequence.

In another embodiment, a method of verifying proper function of a test for detecting and/or classifying a disease or disorder for which manifestation of a methylated gene is a biomarker is provided. The method includes performing a test for detecting, monitoring, or classifying a disease or disorder, or predisposition thereto, for which manifestation of a methylated gene is a biomarker and verifying proper function of the test by performing (e.g. duplicating or repeating) the test utilizing a control that originates from at least one pregnant female animal. The test includes determining the methylation status of at least one biomarker from a biological sample obtained from an animal subject and verifying proper function of the test by performing the test utilizing a control that originates from at least one pregnant female animal.

The at least one agent that provides for determination of a methylation status can be a bisulfite conversion reagent(s). Bisulfite modification of DNA is an art-recognized tool used to assess CpG methylation status. 5-methylcytosine is the most frequent covalent base modification in the DNA of eukaryotic cells. It plays a role, for example, in the regulation of transcription, in genetic imprinting, and in tumorigenesis. Therefore, the identification of 5-methylcytosine as a component of genetic information is of considerable interest. However, 5-methylcytosine positions cannot be identified by sequencing, because 5-methylcytosine has the same base pairing behavior as cytosine. Moreover, the epigenetic information carried by 5-methylcytosine is completely lost during, e.g., PCR amplification. The most frequently used method for analyzing DNA for the presence of 5-methylcytosine is based upon the specific reaction of bisulfite with cytosine whereby, upon subsequent alkaline hydrolysis, cytosine is converted to uracil which corresponds to thymine in its base pairing behavior. Significantly, however, 5-methylcytosine remains unmodified under these conditions. Consequently, the original DNA is converted in such a manner that methylcytosine, which originally could not be distinguished from cytosine by its hybridization behavior, can now be detected as the only remaining cytosine using standard, art-recognized molecular biological techniques, for example, by amplification and hybridization, or by sequencing. All of these techniques are based on differential base pairing properties, which can now be fully exploited.

Another frequently used method for analyzing DNA for the presence of 5-methylcytosine utilizes affinity enrichment of methylated DNA. On example is to enrich methylated DNA by immunoprecipitation with an antibody DNA containing 5-methylcytosine (Weber M, et al., Nat Genet 2005; 37:853-62). Methylated DNA can also be captured on an affinity column or other solid support using a protein that specifically binds double-stranded methylated DNA (Rauch T, et al., Lab Invest 2005; 85:1172-80). These techniques can also be used to isolate, enrich or concentrate DNA containing 5-methylcytosine.

The types of biological samples that can be tested and verified under the methods of the present disclosure are expansive. Non-limiting examples of biological samples include cell lines, histological slides, biopsies, paraffin-embedded tissue, body fluids, stool, colonic effluent, urine, saliva, blood plasma, blood serum, whole blood, isolated blood cells, cells isolated from the blood, and combinations thereof.

The methylated genes that can be biomarkers for a disease or disorder can be selected from known methylated DNA sequences. Non-limiting examples of genes that can be biomarkers for a particular disease or disorder include: SNRPN, SNURF, ABCC6; CA10; DBC2; HEPACAM; HOXB2; HPSE/HPR1; KRT13; MYO3A; NKX6-2; PMF1; POU4F2; SYNPO2/myopodin; ZNF154; 3OST3B; ACADL; ATOH1/hATH; BECN1; C14; CBFA2T3; COL7A1; CREBBP; CXCL1; EDN3; ERBB4/HER4; ETS1; FAM110A/c20; FAM19A4/FLJ25161; FAT4; FGFR4; FOXC1; FOXF1; GHSR; GJB2/CX26; GPR180/ITR; HDAC1; HSD17B1; HSD17B2; HSD17B4; IPF1; ISL1; ITIH5; LEBREL1/P3H2; LEBREL2/P3H3; LRRC49; MGA; miR-124; miR-196a-2; miR-335; MYBL2; NFIX; NRN1; OGG1; PCDHGB6; PPP2R2B; PRDM12; PTRF; RNF20; ST18; STK36; STMN1; SULT1A1; SYNM; THAP10; TOX; TSC1; UAP1L1; UGT3A1; ZBTB8A; ZNF432; ADAMTS12; ADAMTS5; ADHFE1; BARX1; BEND4; CASR; CD109; CDX1; CNR1/CB(1) receptor; CNRIP1; CNTFR; DEXI; DUSP26; EDIL3; ELMO1; EXTL3; EYA2; FLT1; GJC1; GLP1R; GPR101; GRIN2/NMDAR2A; GSPT2; HOMER2; INA; KCNK12; LAMA1; LRP2/megalin; MBD4/MED1; MCC; miR-342; miR-345; NDRG4; NGFR; NR3C1/GR; PIK3CG; PPARG; PTGIS; PTPRR; QKI; RGMA; SEPT9; SPG20; STARD8; STOX2; TBX5; THBS4/TSP4; TMEM8B/NGX6; VSX2/HOX10; ANGTL2; AXIN1; CCBE1; CTGF/IGFBP8; DNAJC15; FBXO32; FILIP1L; FZD4; GPR150; GUCY2C; HOXB5; ITGA8; LRP5; miR-130b; NFATX; PTPRN; RUNX1T1; TERC/hTR; TES; TMCO5; IFFO1; ALK; CHGA; CSMD2; DES; DUSP6; ELOVL4; FANCG; FGF2; FGF3; FGF5; FGF8; FGFR1; FLT3; FLT4; GAS1; GEMIN2/SIP1; HIC2; HSD17B12; IGFBP5; ITPR2; LMO1/RBTN1; I-mfa; miR-132; NEFL; NKX2-8; NTRK3/TRKC; NTSR1; PRG2; PTCH2; SLC32A1; TRH; TUBB3; ZNF415; CLSTN1; HIST1H4K; HIST2H2BF; INHA/inhibin alpha; KCNMA1; NKX3.1; NPBWR1/GPR7; NSMCE1/NSE1; PXMP4/PMP24; RGS2; S100A6; SLC18A2; SPRY4; SVIL; TFAP2E; TGFB2; ZNF132; NFATC; KISS1; CST6; MDFI; ADAM23; ALDH1A3; APC; BNC1; BRCA1; CADM1/TSLC1/IGSF4; CASB; CAV1; CCNA1; CCND2; CD2/SRBC; CD44; CDH1/E-cadherin; CDH13/H-cadherin; CDKN1C/KIP2/p57; CDKN2A/ARF/p14; CDKN2B/INK4B/p15; CHFR; CIDEA; CLSTN1; COL1A2; CYP1A1; DAB2IP; DAPK1; DBC1; DIRAS(3)/ARHI; DKK3; DLC1; DLEC1; DPYS; EOMES; EPHA5; ESR1/ER-alpha; ESR2/ER-beta; FHIT; FHL1; GAS7; GATA5; GSTP1; HIC1; HIST1H4K; HIST2H2Bf; HOXA11; HOXA9; HS3ST2/30ST2; ID4; IGF2; IGFBP3; KCNMA1; LAMA3; LAMC2; MAL; MARVELD1; MDFI; MGMT; MINT1/APBA1; MINT2/APBA2; MINT31; miR-34a; miR-34b; miR-34c; miR-9-1; MLH1; MMP2; MSH2; MSX1; MYOD1/MYF-3; NID2; NKX3-1; NPBWR1; NSMCE1/NSE1; OPCML; p14; PCDH17; PDLIM4/RIL; PENK; PGR; PITX2; PLAU/uPA; PRDM2/RIZ1; PTEN/MMAC1; PTGS2/COX2; PXMP4/PMP24; PYCARD/ASC/TMS1; RARB; RARB2; RARRES1/TIG1; RASSF1; RASSF1A; RASSF2; RB1; RBP1/CRBP1; RGS2; RPIA; RPRM/Reprimo; RUNX3; S100A6; SCGB3A1/HIN1; SERPINB5/maspin; SFN/14-3-3 sigma; SFRP1/SARP2; SFRP2; SFRP4; SFRP5; SLC18A2; SLC5A8; SLIT2; SOCS1; SOX11; SOX17; SPARC; SPOCK2; SPRY4; STK11/LKB1; SVIL; SYK; TCF21; TERT; TFAP2E; TFPI2; TGFB2; THBS1; TIMP3; TMEFF2/HPP1/TPEF; TNFRSF10C/DcR1; TNFRSF10D/DcR2; TNFRSF25/DR3; TWIST1; UCHL1/PGP9.5; VIM; WIF1; WWOX; XAF1; ZNF132; and combinations thereof. Example 4 sets forth a correlation between these genes and the diseases or disorders for which they are biomarkers.

The control composition for use in the methods of the present invention can be made as set forth below. In one embodiment, the control composition can be made by obtaining blood from one or more pregnant female animals, isolating a plasma fraction from the blood, extracting DNA from the plasma fraction, treating the DNA with a reagent or a group of reagents that provides for the determination of the methylation status of said biomarker, and determining the methylation status of said biomarker. In one embodiment, the reagent or group of reagents can include bisulfite conversion reagents or affinity purification reagent(s) such as those discussed above.

The methylated circulating DNA that is present in the control compositions of the present disclosure can originate from a pregnant female animal. In one embodiment, the methylated circulating DNA of the control can originate from at least one pregnant mammal. In another embodiment, the at least one pregnant female animal can be a pregnant human female. In another embodiment, the control can originate from the blood of at least one pregnant female animal.

It has been discovered that methylated DNA sequences are present in the blood of many pregnant female animals. However, while the methylated DNA is present in most subjects, not all pregnant female animals have methylated DNA circulating, thus, in some aspects of the invention, the control containing methylated circulating DNA can be made from a pooling of blood or methylated circulating DNA from a plurality of pregnant female animals, e.g. 10+, 25+, etc. Pooling of the samples from various pregnant female animals can provide for a more uniform and consistent control. The pooling of the blood or methylated DNA can be done at any point during the manufacturing process of the control. For example, if blood is the source of the methylated circulating DNA, the blood of a plurality of pregnant female animals can be pooled and then processed into the control substance. In another embodiment, a plasma fraction containing methylated circulating DNA isolated from the blood of each of a plurality of pregnant female subjects could be pooled after isolation of the plasma fraction. Techniques for isolating a plasma fraction are known in the art and any such technique, such as centrifugation, can be used to isolate the plasma fraction. It has also been noted that the amount of methylated DNA present in the blood of a pregnant female animal tends to increase over the gestational period. Thus, the further along a pregnant female is in her pregnancy, the higher levels of methylated DNA tend to be present in the blood of the subject. Thus, in some embodiments, it can be desirable to have the controls of the present invention originate from pregnant female animals that are in the 2nd half of their gestational period. In another embodiment, when the pregnant female animal is a female a human, it can be useful to have the control originate from that subject during the last two trimesters of the pregnancy, namely, the second or third trimesters.

A method is also provided for of detecting or classifying a disease or disorder or predisposition thereto for which manifestation of a methylated gene is a biomarker. Such a method includes the steps of performing sample testing, confirming proper functioning of the testing by performing the test utilizing the control made by the methods set forth herein, assessing the methylation status of at least one biomarker, and following confirmation of proper function of the test, assigning a diagnosis or prognosis to the animal subject based on the methylation status of the at least one biomarker gene. Sample testing generally includes the steps of identifying a disease, disorder, or predisposition thereto for which manifestation of a methylated gene is a biomarker and selecting at least one corresponding biomarker gene, collecting a biological sample containing DNA from an animal subject, extracting DNA present in the biological sample, treating the DNA with a reagent or group of reagents that provides for the determination of methylation status of the biomarker, and assessing the methylation status of at least one biomarker in the DNA from the biological sample.

A kit for use in testing for cancers having methylated DNA sequences as biomarkers is also provided. In one embodiment, such a kit can include a control containing methylated circulating DNA originating from at least one pregnant female animal and any or all of the following: one or more reagents for extracting DNA, one or more reagents for chemically treating extracted DNA to change the nucleotide sequence of unmethylated DNA sequences, one or more reagents for purifying chemically treated DNA, one or more reagents for purifying chemically treated DNA, or one or more oligonucleotides with functional properties of either a primer capable of amplifying or sequencing a methylated DNA sequence biomarker which is a biomarker for at least one cancer, or a probe capable of detecting a methylated DNA sequence biomarker. An additional kit for use in the detection or quantification of a target nucleic acid in a biological sample is provided that includes a biological sample from a test subject and a control blood sample from at least one pregnant female animal.

In another aspect, the present invention includes an assembly used for the detection or quantification or a target nucleic acid in a biological sample. The assembly, prior to detection or quantification, includes a biological sample from a test subject known to have, or suspected of having a condition for which the target nucleic acid is known to be a biomarker and a control blood sample from at least one pregnant female animal known to contain the target nucleic acid. The target nucleic acid is a gene or a portion of a gene having methylated DNA.

Furthermore, compositions for use as controls for detecting and/or classifying a disease or disorder for which methylated DNA is a biomarker, are also set forth. In one embodiment, compositions for use as controls for detecting, monitoring or classifying diseases, disorders, or predispositions thereto, for which methylated DNA is a biomarker, are also set forth. In one embodiment, the control composition can include a diluent and methylated circulating DNA originating from a pregnant female animal, wherein the methylated circulating DNA is present in the diluent at a concentration of about 1 pg/mL to about 1000 pg/mL. In another embodiment, the composition can include a diluent and methylated circulating DNA that has undergone chemical treatment to change the nucleotide sequence of unmethylated DNA sequences, wherein the circulating DNA is present in the diluent at a concentration of about 1 pg/mL to about 1000 pg/mL. In another embodiment, the composition can include a diluent and methylated circulating DNA that has been isolated from a blood sample from at least one pregnant female animal utilizing one or more reagents for affinity purification and wherein the methylated circulating DNA is present at a concentration of about 1 pg/mL to about 1000 pg/mL. In some embodiments, the concentrations methylated circulating DNA of the above compositions can be from about 5 pg/mL to about 750 pg/mL or about 6 pg/mL to about 500 pg/mL. In one aspect, the control can have a minimum concentration of methylated circulating DNA of at least 6 pg/mL.

The methods, kits and compositions of the present invention can be utilized in the detecting, classifying and/or monitoring, of a variety of diseases and disorders, or the detecting of a predisposition to a disease or disorder, that manifest with methylated genes as a biomarkers. For example, in one embodiment, the disease or disorder can be a cancer. Non-limiting examples of cancers include solid cancers, hematologic cancer, or other malignancies. In another embodiment, the disease or disorder can be a genetic disorder that is manifested by increase in methylation of at least one gene. Non-limiting examples of genetic disorders include Beckwith-Wiedemann syndrome, Prader-Willi syndrome and Angelman's syndrome. In some aspects, a predisposition for a particular disease or disorder can be detected utilizing the methods, kits, and/or compositions of the present disclosure. The disease or disorder for which there is a detected predisposition can include a cancer or an inherited syndrome or disease. Non-limiting examples of such diseases and disorders include the types of cancers and genetic disorders set forth above. Generally, the methods, kits and compositions can be utilized in conjunction with the testing for any cancer or genetic disorder that is manifested by increase in methylation of at least one gene.

EXAMPLES

It should be appreciated by those skilled in the art that the techniques disclosed in the examples which follow represent techniques discovered by the inventors to function well in the practice of the invention, and thus can be considered to constitute particular modes for its practice. However, those of skill in the art should appreciate, in light of the present disclosure, that many changes can be made in the specific embodiments disclosed herein which will still obtain a like or similar result without departing from the spirit and scope of the invention.

Example 1

Preparation of Control Composition with SEPT9 Methylated DNA

The SEPT9 biomarker assay is used to identify presence or absence of SEPT9 methylated DNA in plasma. There are four parts to the assay: DNA isolation from plasma, bisulfite conversion, bisulfite purification, and real-time PCR. Positive control is made from a uniform, or substantially uniform mixture of plasma from pregnant women that is aliquoted for single use. One aliquot is processed alongside the patient samples each time the assay is run to ensure the entire process is working properly.

The positive control composition is prepared utilizing whole blood from twenty-five pregnant women in their second into their third trimester and is placed in two 10 mL EDTA tubes. The whole blood from each woman is spun in the tubes at 1350×g for twelve minutes following which the plasma is removed without disturbing the buffy coat and transferred to clean 15 mL conical tubes. The plasma is then spun a second time at 1350×g for twelve minutes after which the plasma is removed without disturbing the pellet. The plasma from each of the 50 tubes (two tubes for each woman) is then pooled and mixed to ensure a uniform or substantially uniform solution. The pooled plasma is aliquoted into 4 mL aliquots and frozen at −70° C. until it is too be used.

Example 2

Testing of Pooled Plasma for Use as Control for SEPT9 Detection

Pooled plasma from Example 1 was tested for its effectiveness as described herein. One aliquot of the pooled plasma was thawed and was then extracted using the Chemagic NA Extraction Kit (Chemagen, Cat #1045) following the product insert protocol. The DNA is eluted in 100 µL of elution buffer. After DNA extraction, the samples are treated with bisulfite conversion reagents prepared according to the protocol in the supplementary information set forth in the publication by deVos et al. entitled *Methylated circulating SEPT9 DNA in plasma is a biomarker for colorectal cancer. Clin Chem.* 2009, 55:1337-46, which is hereby incorporated by reference. Volumes and cycling conditions are also according to the teachings of deVos et al.

Following bisulfite conversion, the samples were purified using the Chemagic Bisulfite Purification Ki (Chemagen, cat 1036) following the product insert protocol. The DNA was eluted in 55 µL of elution buffer. A multiplexed real-time PCR with SEPT9 and ACTB is performed on each sample in triplicate. The final PCR volume is 25 µL with 10 µL bisulfite converted DNA and 12.5 µL 2× QuantiTect Multiplex Kit No. ROX (Qiagen, cat #45554). The sequences and final concentrations of primers and probes are as follows: SEPT9-FWD AAATAATCCCATCCAACTA (1.5 µM) (SEQ ID. NO 1), SEPT9-REV GATT-dSp-GTTGTTTATT AGTTATTATGT (1.5 µM) (SEQ ID. NO 2), SEPT9-blocker GTTATTATGTTGGATTTTGTGGTTAATGTGTAG-SpC3 (1.0 µM) (SEQ ID. NO 3), SEPT9-Probe FAMTTAACCGC-GAAATCCGAC-BHQ1 (0.075 µM) (SEQ ID. NO 4), ACTB-FWD GTGATGGAGGAGGTTTAGTAAGTT (0.2 µM) (SEQ ID. NO 5), ACTB-REV CCAATAAAAC-CTACTCCTCCCTTAA (0.2 µM) (SEQ ID. NO 6), ACTB-probe TEX615ACCACCACCCAACA-CACAATAACAAACACA-IAbrQSp (0.75 µM) (SEQ ID. 7). Real-time PCR was performed on the LC480 thermal cycler (Roche Applied Systems) using the following cycling conditions: activation at 95° C. for 30 minutes, 50 cycles of 95° C. for 10 seconds, 56° C. 30 seconds, and final cooling to 40° C. for 30 seconds. Heating rate were 4.4° C./second and cooling rates were 2.2° C./second. Data was acquired at the end of each 56° C. step. Samples were analyzed using the ABsQuant/$2^{nd}$ DerivativeMax function of the LC480 software.

Example 3

IFFO1 Methylated DNA Detection by Real-Time PCR

The specimens used were 10 pregnant women and 16 negative controls, males under the age of 30. Two plasma tubes from each specimen were used. Each plasma tube was prepared differently. One tube was spun once with one plasma transfer. The second tube was spun twice with two plasma transfers. The DNA was extracted from 4 mL of plasma using the Perkin-Elmer Chemagen NA Extraction Kit following the product insert protocol. The DNA was then bisulfite converted using the method described in the deVos et al publication set forth in Example 2. Bisulfite purification was completed using a Perkin-Elmer Chemagen Bisulfite Purification Kit following the product insert protocol. The final elution volume was 55 µL. Three 10 µL reactions were done for SEPT9 methylated DNA detection by real-time PCR. The remaining 25 µL were used for two 10 µL reactions for IFFO1 methylated DNA detection by real-time PCR.

The PCR is a Multiplex with an internal control gene to verify DNA extraction and bisulfite conversion. The same ACTB fragment and probe dye were the same as those used in Example 2. The PCR master mix includes was as follows:

12.5 μL Quantitect Multiplex No ROX kit (Qiagen #204745), 1 μL IFFO1 primer/blocker mix, 1 μL ACTB primer mix, 0.5 μL IFFO1/ACTB probe mix, 10 μL extracted DNA. The cycling conditions used were cycling conditions on LC480: 95° C. for 30 minutes; 95° C. for 15 seconds, 50 cycles; 60° C. for 60 seconds; 40° C. for 30 seconds. The following table is a list of the primer/probe sequences, gene type and final PCR primer/probe concentrations.

TABLE I

| Primer Sequence | | Final PCR Concentration |
|---|---|---|
| IFFO1 FWD: TCGAATAACGGATTTATGGTTGC (SEQ. ID. NO. 7) | Gene of Interest | 1.5 μM |
| IFFO1 REV: GCCGCATTAACTCTTCTAACTCG (SEQ. ID. NO. 8) | Gene of Interest | 1.5 μM |
| IFFO1 Probe: /56-FAM/CCCTACTCCTACACCGATCTACATCTCCCAA/3IABkFQ/(SEQ. ID. NO. 9) | Gene of Interest | 0.075 μM |
| IFFO1 Blocker REV: ACATTAACTCTTCTAACTCACCTTCCATCCCTACTC CTACACCA/3SpC3/(SEQ. ID. NO. 10) | Gene of Interest | 1.0 μM |
| ACTB FWD: GTGATGGAGGAGGTTTAGTAAGTT (SEQ. ID. NO. 11) | Control Gene | 0.075 μM |
| ACTB REV: CCAATAAAACCTACTCCTCCCTTAA (SEQ. ID. NO. 12) | Control Gene | 0.075 μM |
| ACTB Probe: /5TEX615/ACCACCACCCAACACACAATAACAAACA CA/3IAbRQSp/(SEQ. ID. NO. 13) | Control Gene | 0.075 μM |

Raw data from the pregnant women for the genes of interest as well as the ACTB control gene are provided in Table II while a summary of the pregnant women for the gene of interest and the ACTB control gene is provided in Table III.

TABLE II

| Pos | Name | IFFO1 Cp 1 | IFFO1 Cp 2 | Ave IFFO1 Cp | ACTB Cp 1 | ACTB Cp 2 | Ave ACTB Cp |
|---|---|---|---|---|---|---|---|
| A1 | PWS-001.1 | | | | 29.23 | 29.07 | 29.2 |
| B1 | PWS-001.2 | | | | 29.7 | 29.81 | 29.8 |
| C1 | PWS-002.1 | 38.88 | 38.27 | 38.6 | 28.52 | 28.55 | 28.5 |
| D1 | PWS-002.2 | 42.46 | 41.14 | 41.8 | 28.99 | 29.02 | 29.0 |
| G1 | PWS-003.1 | 37.57 | 38.14 | 37.9 | 28.93 | 28.91 | 28.9 |
| H1 | PWS-003.2 | 38.03 | 37.85 | 37.9 | 29.15 | 29.19 | 29.2 |
| A3 | PWS-004.1 | 36.9 | 37.64 | 37.3 | 27.34 | 27.52 | 27.4 |
| B3 | PWS-004.2 | 38.27 | 39.17 | 38.7 | 29.11 | 29 | 29.1 |
| E3 | PWS-005.1 | 37.03 | 37.95 | 37.5 | 29.11 | 29.1 | 29.1 |
| F3 | PWS-005.2 | 37.85 | 39.16 | 38.5 | 29.53 | 29.55 | 29.5 |
| G3 | PWS-006.1 | 40.31 | | 40.3 | 28.64 | 28.7 | 28.7 |
| H3 | PWS-006.2 | 41.58 | 38.91 | 40.2 | 29.79 | 29.81 | 29.8 |
| C5 | PWS-007.1 | 38.04 | 37.5 | 37.8 | 26.17 | 26.17 | 26.2 |
| D5 | PWS-007.2 | 37.82 | 37.22 | 37.5 | 26.44 | 26.35 | 26.4 |
| E5 | PWS-008.1 | 38.92 | 39.48 | 39.2 | 28.71 | 28.75 | 28.7 |
| F5 | PWS-008.2 | 38.81 | 40.58 | 39.7 | 29.64 | 29.72 | 29.7 |
| A7 | PWS-009.1 | 37.94 | 39.51 | 38.7 | 29.15 | 29.13 | 29.1 |
| B7 | PWS-009.2 | 37.96 | 38.11 | 38.0 | 29.93 | 29.99 | 30.0 |
| C7 | PWS-010.1 | | 40.83 | 40.8 | 29.23 | 29.24 | 29.2 |
| D7 | PWS-010.2 | | | | 29.83 | 29.93 | 29.9 |

TABLE III

| | 1 spin number of PCR pos out of 2 | 2 spin number of PCR pos out of 2 |
|---|---|---|
| PWS-001 | 0 | 0 |
| PWS-002 | 2 | 2 |
| PWS-003 | 2 | 2 |
| PWS-004 | 2 | 2 |

TABLE III-continued

| | 1 spin number of PCR pos out of 2 | 2 spin number of PCR pos out of 2 |
|---|---|---|
| PWS-005 | 2 | 2 |
| PWS-006 | 1 | 2 |
| PWS-007 | 2 | 2 |
| PWS-008 | 2 | 2 |
| PWS-009 | 2 | 2 |
| PWS-010 | 1 | 0 |

As shown in the data of Tables II and III, 7 out of 10 pregnant women had 2 IFFO1 PCRs detected in both 1 and 2 spins and 1 out of 10 had 1 PCR in the one spin and 2 PCRs in the 2 spin. One sample had 1 PCR in 1 spin only and one sample had no detectable IFFO1. Taking each extraction as its own sample, 17 out of 20 samples had IFFO1 methylated DNA detected for a total sensitivity of 85%. If both the spins out of the 10 samples were to be required to have detectable IFFO1 methylated DNA, 8 out of 10 specimens would be considered to be positive, resulting in a sensitivity of 80%.

Raw data from the negative control males for the genes of interest as well as the control gene are provided in Table IV while a summary of the negative control males for the gene of interest and the ACTB control gene is provided in Table V.

TABLE IV

| Pos Name | IFFO1 Cp 1 | IFFO1 Cp 2 | Ave IFFO1 Cp | ACTB Cp 1 | ACTB Cp 2 | Ave ACTB Cp |
|---|---|---|---|---|---|---|
| A1 CTRL-001.1 | 39.62 | 42.47 | 41.0 | 28.49 | 28.62 | 28.6 |
| B1 CTRL-001.2 | | | | 29.5 | 29.57 | 29.5 |
| C1 CTRL-002.1 | 41.14 | | 41.1 | 28.11 | 28.08 | 28.1 |
| D1 CTRL-002.2 | | | | 28.32 | 28.42 | 28.4 |
| E1 CTRL-003.1 | | | | 27.93 | 27.98 | 28.0 |
| F1 CTRL-003.2 | | | | 28.89 | 29.04 | 29.0 |
| G1 CTRL-004.1 | | | | 25.85 | 25.93 | 25.9 |
| H1 CTRL-004.2 | | | | 30.48 | 30.53 | 30.5 |
| A3 CTRL-005.1 | | | | 27.9 | 27.94 | 27.9 |
| B3 CTRL-005.2 | | | | 28.33 | 28.5 | 28.4 |
| C3 CTRL-006.1 | | 39.9 | 39.9 | 28.51 | 28.44 | 28.5 |
| D3 CTRL-006.2 | | | | 28.85 | 28.86 | 28.9 |
| E3 CTRL-007.1 | 40.63 | 40.12 | 40.4 | 27.49 | 27.31 | 27.4 |
| F3 CTRL-007.2 | | 39.94 | 39.9 | 28.07 | 27.99 | 28.0 |
| A5 CTRL-008.1 | | | | 29.12 | 29.1 | 29.1 |
| B5 CTRL-008.2 | | | | 29.85 | 29.92 | 29.9 |
| C5 CTRL-009.1 | | | | 29.08 | 29.1 | 29.1 |
| D5 CTRL-009.2 | | | | 29.68 | 29.62 | 29.7 |
| E5 CTRL-010.1 | 40.21 | | 40.2 | 28 | 28.08 | 28.0 |
| F5 CTRL-010.2 | 39.94 | 39.9 | 39.9 | 28.44 | 28.52 | 28.5 |
| G5 CTRL-011.1 | | | | 28.61 | 28.73 | 28.7 |
| H5 CTRL-011.2 | | | | 29.06 | 29.15 | 29.1 |
| A7 CTRL-012.1 | 44.08 | | 44.1 | 26.62 | 26.66 | 26.6 |
| B7 CTRL-012.2 | | | | 28.06 | 28.17 | 28.1 |
| C7 CTRL-013.1 | | | | 29.56 | 29.51 | 29.5 |
| D7 CTRL-013.2 | | | | 30.49 | 30.49 | 30.5 |
| E7 CTRL-014.mixed | | | | 29.96 | 29.93 | 29.9 |
| F7 CTRL-014.mixed | | | | 30.02 | 29.82 | 29.9 |
| G7 CTRL-015.1 | | | | 28.95 | 29.1 | 29.0 |
| H7 CTRL-015.2 | | | | 29.55 | 29.75 | 29.7 |
| A9 CTRL-016.1 | 40.43 | | 40.4 | 28.7 | 28.69 | 28.7 |
| B9 CTRL-016.2 | | | | 29.64 | 29.62 | 29.6 |

TABLE V

| | 1 spin number of PCR pos out of 2 | 2 spin number of PCR pos out of 2 | Comments |
|---|---|---|---|
| CTRL-001 | 2 | 0 | |
| CTRL-002 | 1 | 0 | |
| CTRL-003 | 0 | 0 | |
| CTRL-004 | 0 | 0 | |
| CTRL-005 | 0 | 0 | |
| CTRL-006 | 1 | 0 | |
| CTRL-007 | 2 | 1 | |
| CTRL-008 | 0 | 0 | |
| CTRL-009 | 0 | 0 | |
| CTRL-010 | 1 | 2 | |
| CTRL-011 | 0 | 0 | |
| CTRL-012 | 1 | 0 | |
| CTRL-013 | 0 | 0 | |
| CTRL-014 | 0 | 0 | mixed |
| CTRL-015 | 0 | 0 | |
| CTRL-016 | 1 | 0 | |

As can be seen in Tables IV and V, 2 out of 16 controls have both 1 spin and 2 spin with detectable IFFO1. 5 other 1 spin samples have detectable IFFO1. There are no 2 spin with detectable IFFO1 other than the two with 1 spin detected. Taking each extraction as its own sample, 9 out of 32 negative control samples had IFFO1 methylated DNA detected for a total specificity of 71.9%. If both the spins out of the 10 samples were to be required to have detectable IFFO1 methylated DNA, 2 out of 16 negative control specimens were positive, resulting in a specificity of 88.5%.

Example 4

Additional Diseases or Disorders that Manifest with Methylated DNA

Pooled plasma of pregnant women can be prepared as described in Example 1 to act as a control for other diseases or disorders that manifest with methylated DNA. Examples of such genes, their UniGene ID numbers, and the associated disease or disorders are set forth in Tables VI-XIII below.

TABLE VI

Methylated biomarkers for bladder cancer

| Gene | UniGene UGID | Reference | Specimen Types |
|---|---|---|---|
| ABCC6 | 237219 | Yu J, 2007 | Tissue, urine sediment |
| CA10 | 678625 | Chung W, 2011 | Tissue, urine sediment |
| DBC2 | 199978 | Shi Y, 2008 | Tissue |
| HEPACAM | 238206 | Pan C, 2010 | Tissue |
| HOXB2 | 255815 | Marsh CJ, 2010 | Tissue |
| HPSE/HPR1 | 137179 | Yu J, 2007 | Tissue, urine sediment |
| KISS1 | 141712 | Cebrian V, 2011 | |
| KRT13 | 2723868 | Marsh CJ, 2010 | Tissue |
| MYO3A | 2731948 | Chung W, 2011 | Tissue, urine sediment |
| NKX6-2 | 150031 | Chung W, 2011 | Tissue, urine sediment |
| PMF1 | 1204746 | Aleman A, 2008 | Tissue |
| POU4F2 | 130715 | Reinert T, 2011 | Tissue, urine sediment |
| SYNPO2/myopodin | 2724837 | Cebrian V, 2008; Alvarex-Mugica M, 2010 | Tissue, urine sediment |
| ZNF154 | 2477002 | Reinert T, 2011 | Tissue, urine sediment |

TABLE VII

Methylated biomarkers for breast cancer

| Gene | UniGene UGID | Reference | Specimen Types |
|---|---|---|---|
| 3OST3B | 137646 | Chen CB, 2003 | Tissue |
| ACADL | 686436 | Hill VK, 2011 | Tissue |
| ATOH1/hATH | 1292055 | Ordway JM, 2007 | Tissue |
| BECN1 | 3615981 | Li Z, 2010 | Tissue |
| C14orf21 | NC_018925 (Alternate ID) | Chan TA, 2008 | Tissue |
| CBFA2T3 | 904558 | Bais AJ, 2004 | |
| COL7A1 | 904558 | Chan TA, 2008 | Tissue |
| CREBBP | 674918 | Rooneberg JA, 2011 | Tissue |
| CST6 | 150957 | Radpour R, 2009 | |
| CXCL1 | 130839 | Ordway JM, 2007 | Tissue |
| EDN3 | 130995 | Wiesmann F, 2009 | Tissue |
| ERBB4/HER4 | 208580 | Das PM, 2010 | Tissue |
| ETS1 | 198085 | Ronneberg JA, 2011 | Tissue |
| FAM110A/c20orF55 | 1847809 | Hartmann O, 2009 | Tissue |
| FAM19A4/FLJ25161 | 160010 | Miyamoto K, 2005 | Tissue |
| FAT4 | 1778725 | Qi C, 2009 | Tissue |
| FGFR4 | 157049 | Zhu X, 2010 | Tissue |
| FOXC1 | 193592 | Dejeux E, 2010; Muggerud AA, 2010 | Tissue |
| FOXF1 | 154531 | Lo PK, 2010 | Tissue |
| GHSR | 426873 | Ordway JM, 2007 | Tissue |
| GJB2/CX26 | 915641 | Miyamoto K, 2005 | Tissue |
| GPR180/ITR | 234400 | Hill VK, 2011 | Tissue |
| HDAC1 | 141178 | Ronneberg JA, 2011 | Tissue |

TABLE VII-continued

Methylated biomarkers for breast cancer

| Gene | UniGene UGID | Reference | Specimen Types |
|---|---|---|---|
| HSD17B1 | 2723703 | Bhavani V, 2009 | Tissue |
| HSD17B2 | 156469 | Bhavani V, 2009 | Tissue |
| HSD17B4 | 220332 | Muller HM, 2003; Muller HM, 2004; Fiegl H, 2006 | Tissue, serum |
| IPF1 | 136125 | Ronneberg JA, 2011 | Tissue |
| ISL1 | 130773 | Ronneberg JA, 2011 | Tissue |
| ITIH5 | 713745 | Veeck J, 2008; Veeck J, 2008 | Tissue |
| LEBREL1/P3 H2 | 200587 | Shah R, 2009 | Tissue |
| LEBREL2/P3 H3 | 2138549 | Shah R, 2009 | Tissue |
| LRRC49 | 132969 | De Souza Santos, 2008 | Tissue |
| MGA | 159933 | Ordway JM, 2007 | Tissue |
| miR-124a3 | NA | Lehmann U, 2008; Lehmann U, 2008 | Tissue |
| miR-196a-2 | 31568 (Alternate ID HGNC) | Hoffman AE, 2009 | Tissue |
| miR-335 | 31773 (Alternate ID HGNC) | PngKJ, 2011 | Tissue |
| MYBL2 | 159026 | Ronneberg JA | Tissue |
| NFIX | 171397 | Ordway JM, 2007 | Tissue |
| NRN1 | 143155 | Kim JH, 2011 | Tissue |
| OGG1 |  | Ronneberg JA, 2011 | Tissue |
| PCDHGB6 | 197358 | Miyamoto K, 2005 | Tissue |
| PPP2R2B | 2724531 | Dejeux E, 2010; Muggerud AA, 2010; Tan J, 2010 | Tissue |
| PRDM12 | 710470 | Ordway JM, 2007 | Tissue |
| PTRF | 232228 | Bai L, 2011 | Tissue |
| RNF20 | 262253 | Shema E, 2008 | Tissue |
| ST18 | 2724817 | Jandrig B, 2004 | Tissue |
| STK36 | 686563 | Ordway JM, 2007 | Tissue |
| STMN1 | 163973 | Golouh R, 2008 | Tissue |
| SULT1A1 | 1782831 | Kwon MS, 2006; Kim SJ, 2010 | Tissue |
| SYNM | 163311 | Noetzel E, 2010 | Tissue |
| THAP10 | 2060134 | De Souza Santos, 2008 | Tissue |
| TOX | 139396 | Chung W, 2008 | Tissue |
| TSC1 | 198907 | Jiang WG, 2005 | Tissue |
| UAP1L1 | 151085 | Hill VK, 2011 | Tissue |
| UGT3A1 | 170712 | Hill VK, 2011 | Tissue |
| ZBTB8A | 1414772 | Ordway JM, 2007 | Tissue |
| ZNF432 | 2725252 | Chan TA, 2008 | Tissue |

TABLE VIII

Methylated biomarkers for colorectal cancer

| Gene | UniGene UGID | Reference | Specimen Types |
|---|---|---|---|
| ADAMTS12 | 14605 (Alternate, HGNC ID) | Moncada-Pazos A 2009 |  |
| ADAMTS5 | 138487 | Kim YH, 2011 |  |
| ADHFE1 | 3879802 | Kim YH 2011; Oster B, 2011 |  |
| BARX1 | 156907 | Kober P, 2011 |  |
| BEND4 | 145716 | Mori Y, 2011 | Tissue |
| CASR | 230652 | Hizaki K, 2011 |  |
| CD109 | 215622 | Mokarram P, 2009 |  |
| CDX1 | 131029 | Pilozzi, 2004; Xu XL, 2004 |  |
| CNR1/CB(1) receptor | 139732 | Wang D, 2008; Gustafsson, 2011 |  |
| CNRIP1 | 164677 | Lind GE, 2011; Oster B, 2011 |  |
| CNTFR | 148614 | Kober P, 2011 |  |
| DEXI | LOC100289656 (Alternate ID) | Miyaki Y, 2012 |  |
| DUSP26 | 132386 | Kaneda A, 2011 |  |
| EDIL3 | 697889 | Kaneda A, 2011 |  |
| ELMO1 | 230026 | Yagi K, 2010 |  |
| EXTL3 | 706513 | Karibe T, 2008 |  |
| EYA2 | 688036 | Zou H, 2007 |  |
| FLT1 | 2063465 | Hinoue T, 2009 | Tissue |
| GJC1 | 1281431 | Ahmed D, 2011; Mori Y, 2011; Sirnes S, 2011 |  |
| GLP1R | 207639 | Mori, 2011 | Tissue |
| GPR101 | 193798 | Kober P, 2011 |  |
| GRIN2/NMDAR2A | 914122 | Kim S, 2008 |  |
| GSPT2 | 138636 | Kober P, 2011 |  |
| HOMER2 | 1851430 | Mori Y, 2011 | Tissue |
| NA | 716075 | Lind GE, 2011 |  |
| KCNK12 | 2060597 | Kober P, 2011 |  |
| LAMA1 | 173000 | Kim YH, 2011 |  |
| LRP2/megalin | 2727047 | Kondo Y, 2004 |  |
| MBD4/MED1 | 136379 | Howard JH, 2009 |  |
| MCC | 2062182 | Kohonen-Corish MR, 2007; Fukuyama R, 2008 |  |
| miR-342 | 31778 (Alternate HGNC ID) | Grady WM, 2008 |  |
| miR-345 | 31779 (Alternate HGNC ID) | Tang JT, 2011 |  |
| NDRG4 | 186867 | Melotte, 2009 |  |
| NGFR | 222822 | Lofton-Day C, 2008 |  |
| NR3C1/GR | 146366 | Lind GE 2006; Ahlquist T, 2008 |  |
| PIK3CG | 136126 | Semba, 2002 |  |
| PPARG | 156431 | Pancione M, 2010 |  |
| PTGIS | 181376 | Frigola, 2005 |  |
| PTPRR | 721235 | Menigatti m, 2009 |  |
| QKI | 725483 | Yang G, 2010 |  |
| RGMA | 173188 | Li Vs, 2009 |  |
| SEPT9 | 173188 | Lofton-Day, 2008; Grutzmarm, 2008; deVos, 2009; He Q, 2010; Kostin PA | Tissue, plasma |
| SPG20 | 235451 | Lind GE, 2011 |  |
| STARD8 | 141720 | Mokarram P, 2009 |  |
| STOX2 | 2977262 | Kaneda |  |
| TBX5 | 204359 | Yu J, 2010 |  |
| THBS4/TSP4 | 164304 | Greco, 2010 | Tissue |
| TMEM8B/NGX6 | 708967 | Liu M, 2010 | Tissue |
| VSX2/HOX10 | 618734 | Mori Y, 2011 | Tissue |

TABLE IX

Methylated biomarkers for ovarian cancer

| Gene | UniGene UGID | Reference | Specimen Types |
|---|---|---|---|
| ANGTL2 | 2619684 | Kikuchi R, 2008 | Tissue |
| AXIN | 2061093 | Dai W, 2011 | Tissue |
| CCBE | 136258 | Barton, CA | Tissue |
| CTGF/IGFBP8 | 221471 | Kikuchi R, 2007 | Tissue |
| DNAJC15 | 233867 | Hatle KM, 2007 | Tissue |
| FBXO32 | 218285 | Chou JL 2010; Yeh KT, 2011 | Tissue. |
| FILIP1L | 143343 | Burton ER, 2011 | Tissue |
| FZD4 | 2060979 | Dai W, 2011 | Tissue |
| GPR150 | 151200 | Cai Ly, 2007 | Tissue |

TABLE IX-continued

Methylated biomarkers for ovarian cancer

| Gene | UniGene UGID | Reference | Specimen Types |
|---|---|---|---|
| GUCY2C | 915025 | Bauerschlag DO, 2011 | Tissue |
| HOXBS | 255815 | Wu Q, 2007 | Tissue |
| ITGA8 | 157992 | Cai LY, 2007 | Tissue |
| LRPS | 131846 | Dai W, 2011 | Tissue |
| miR-130b | 31515 (Alternate HGNC ID) | Yang C, 2011 | Tissue |
| NFATC | 1350811 | Dai W, 2011 | Tissue |
| PTPRN | 141295 | Bauerschlag DO, 2011 | Tissue |
| RUNX1T1 | 197528 | Yeh KT, 2011 | Tissue |
| TERC/hTR | 231219 | Strathdee G, 2001 | Tissue |
| TES | 2061297 | Qui H, 2010 | Tissue |
| TMCOS | 287284 | Bauerschlag DO, 2011 | Tissue |
| IFFO1 | 133401 | Campan M, 2011 | |

TABLE X

Methylated biomarkers for pancreatic cancer

| Gene | UniGene UGID | Reference | Specimen Types |
|---|---|---|---|
| ALK | 2723787 | Tan AC, 2009 | Tissue |
| CHGA | 153824 | Tan AC, 2009 | Tissue |
| CSMD2 | 2726233 | Shimizu H, 2011 | Tissue |
| DES | 2063963 | Tan AC, 2009 | Tissue |
| DUSP6 | 180786 | Xu S, 2005 | Tissue |
| ELOVL4 | 142985 | Omura N, 2008 | Tissue |
| FANCG | 2060095 | Tan AC, 2009 | Tissue |
| FGF2 | 177026 | Tan AC, 2009 | Tissue |
| FGF3 | 136496 | Tan AC, 2009 | Tissue |
| FGFS | 136493 | Tan AC, 2009 | Tissue |
| FGF8 | 138391 | Tan AC, 2009 | Tissue |
| FGFR1 | 172147 | Tan AC, 2009 | Tissue |
| FLT3 | 722749 | Tan AC, 2009 | Tissue |
| FLT4 | 2477541 | Tan AC, 2009 | Tissue |
| GAS1 | 139067 | Tan AC, 2009 | Tissue |
| GEMIN2/SIP1 | 2559280 | Li A, 2010 | Tissue |
| HIC2 | 2139661 | Tan AC, 2009 | Tissue |
| HSD17B12 | 149624 | Tan AC, 2009 | Tissue |
| IGFBPS | 2076223 | Tan AC, 2009 | Tissue |
| ITPR2 | 902982 | Tan AC, 2009 | Tissue |
| LMO1/RBTN1 | 2723744 | Tan AC, 2009 | Tissue |
| MDFI | 910866 | Omura N, 2008 | Tissue |
| miR-132 | 31516 (Alternate HGNC ID) | Zhang S, 2011 | Tissue |
| NEFL | 912208 | Tan AC, 2009 | Tissue |
| NKX2-8 | 167403 | Hagihara A, 2004 | Tissue |
| NTRK3/TRKC | 221697 | Tan AC, 2009 | Tissue |
| NTSR1 | 2059880 | Hagihara A, 2004 | Tissue |
| PRG2 | 903380 | Hagihara A, 2004 | Tissue |
| PTCH2 | 2060508 | Tan AC, 2009 | Tissue |
| SLC32A1 | 158967 | Shimizu H, 2011 | Tissue |
| TLL1 | 143679 | Hagihara A, 2004 | |
| TRH | 5796694 | Shimizu H, 2011 | Tissue |
| TUBB3 | 902490 | Tan AC, 2009 | Tissue |
| ZNF415 | 152782 | Omura N, 2008 | Tissue |

TABLE XI

Methylated biomarkers for prostate cancer

| Gene | UniGene UGID | Reference | Specimen Types |
|---|---|---|---|
| CLSTN1 | 135691 | Kwabi-Addo B, 2007; Chung W, 2008 | Tissue |
| HIST1H4K | 1097005 | Payne SR, 2009 | Urine |
| HIST2H2BF | 2139345 | Weiss G, 2009 | Tissue |
| INHA/inhibin alpha | 220636 | Schmitt JF, 2002 | Tissue |
| KCNMA1 | 151586 | Vanaja DK, 2009 | Tissue |
| NKX3.1 | 138307 | Astiani E, 2005; Kunderfranco P, 2005 | Tissue |
| NPBWR1/GPR7 | 169030 | Cottrell S, 2007 | Tissue |
| NSMCE1/NSE1 | 177053 | Chung W, 2008 | Tissue |
| PXMP4/PMP24 | 2724175 | Zhang X, 2010 | Tissue |
| RGS2 | 140287 | Wolff DW, 2011 | Tissue |
| S100A6 | 173957 | Rehman I 2004; Rehman I, 2005 | Tissue |
| SLC18A2 | 2066003 | Sorensen KD, 2009 | Tissue |
| SPRY4 | 187066 | Wang J, 2006 | Tissue |
| SVIL | 714368 | Vanaja DK, 2006 | Tissue |
| TFAP2E | 1783333 | Payne SR, 2009 | Tissue, plasma, urine |
| TGFB2 | 149923 | Liu L, 2011 | Tissue |
| ZNF132 | 154645 | Abildgaard MO, 2011 | Tissue |

TABLE XII methylated biomarkers that are common for multiple cancers

| Gene | UniGene UGID | Reference | Sample Type |
|---|---|---|---|
| ADAM23 | 2060654 | Hagihara A, 2004 | |
| ALDH1A3 | 674697 | Shames, 2006 | |
| APC | 155479 | Hiltunen, 1997 | Tissue, stool, blood |
| BNC1 | 674312 | Shames, 2006 | |
| BRCA1 | 161154 | Dobrovic A, 1997 | |
| CADM1/TSLC1/IGSF4 | 198722 | Allinen A, 2002 | |
| CASB | 131185 | | |
| CAV1 | 139632 | Cui J, 2001 | |
| CCNA1 | 223227 | Shames, 2006 | |
| CCND2 | 201376 | Evron E, 2001 | |
| CD2/SRBC | 914247 | Tong SY, 2010 | |
| CD44 | 717487 | Lou W, 1999 | |
| CDH1/E-cadherin | 676245 | Wheeler, 2001 | |
| CDH13/H-cadherin | 2723704 | Kawakami M, 1999 | |
| CDKN1C/KIP2/p57 | 143634 | Lodygin D, 2005 | |
| CDKN2A/ARF/p14 | 903346 | Silva J, 2001 | |
| CDKN2B/INK4B/p15 | 139517 | Liu Z 2005 | |
| CHFR | 3879976 | Corn, 2003 | |
| CIDEA | 169236 | Hill VK, 2010 | |
| CLSTN1 | 135691 | Kwabi-Addo B, 2007 | |
| COL1A2 | 704301 | Sengupta PK, 2003 | |
| CYP1A1 | 139520 | Okino ST, 2006 | |
| DAB2IP | 913125 | Dote H, 2004 | |
| DAPK1 | 203640 | Müller HM, 2003 | |
| DBC1 | 1272214 | Tan AC, 2009 | |
| DIRAS(3)/ARHI | 161252 | Yuan J, 2003 | |
| DKK3 | 179404 | Lodygin D, 2005 | |
| DLC1 | 150104 | Teramoto A, 2004 | |
| DLEC1 | 3370079 | Kwong J, 2006 | |
| DPYS | 238198 | Chung W, 2008 | |
| EOMES | 2060674 | Reinert T, 2011 | |
| EPHAS | 2723810 | Tan AC, 2009 | |
| ESR1/ER-alpha | 163517 | Piva R, 1990 | stool |
| ESR2/ER-beta | 2729925 | Zhao C, 2003 | |
| FHIT | 2725313 | Maruyama R, 2001 | |
| FHL1 | 230406 | Li X, 2008 | |

TABLE XII-continued methylated biomarkers that are common for multiple cancers

| Gene | UniGene UGID | Reference | Sample Type |
|---|---|---|---|
| GAS7 | 677373 | Tan AC, 2009 | |
| GATA5 | 194343 | Akiyama, 2003 | |
| GSTP1 | 914583 | Lee Wh, 1994 | |
| HIC1 | 139530 | Fujii H, 1998 | |
| HIST1H4K | 1097005 | Payne SR, 2009 | |
| HIST2H2Bf | 2139345 | Weiss G, 2009 | |
| HOXA11 | 169245 | Fiegl H, 2008 | |
| HOXA9 | 2728668 | Reynolds PA, 2006 | |
| HS3ST2/30ST2 | 144701 | Miyamoto K, 2003 | |
| ID4 | 910348 | Umetani, 2004 | |
| IGF2 | 173422 | Issa JP, 1996 | |
| IGFBP3 | 619193 | Huang Z, 2006 | |
| KCNMA1 | 151586 | Vanaja DK, 2009 | |
| LAMA3 | 231404 | Sathyanarayana UG, 2003 | |
| LAMC2 | 2060495 | Sathyanarayana UG, 2003 | |
| MAL | 140461 | Lind, 2008 | |
| MARVELD1 | 163892 | Wang S, 2009 | |
| MDFI | 910866 | Omura N, 2008 | |
| MGMT | 716601 | Estellar M, 2001 | |
| MINT1/APBA1 | 158135 | Toyota M, 1999 | |
| MINT2/APBA2 | 2087123 | Toyota M, 1999 | |
| MINT31 | NA | Toyota M, 1999 | |
| miR-34a | HGNC:31635 | Strathdee G, 2001 | |
| miR-34b | HGNC:31636 | Toyota, 2008 | stool |
| miR-34c | HGNC:31637 | Toyota, 2008 | stool |
| miR-9-1 | HGNC:31641 | Omura N, 2008 | |
| MLH1 | 161374 | Strathdee G, 2001 | |
| MMP2 | 904364 | Shukeir N, 2006 | |
| MSH2 | 2066667 | Naqvi RA, 2008 | |
| MSX1 | 225211 | Shames DS, 2006 | |
| MY0D1/MYF-3 | 159276 | Hahnel R, 1996 | |
| NID2 | 198326 | Ulazzi, 2007 | |
| NKX3-1 | 138307 | Asatiani E, 2005 | |
| NPBWR1 | 169030 | | |
| NSMCE1/NSE1 | 177053 | Chung W, 2008 | |
| OPCML | 131557 | Sellar GC, 2003 | |
| p14 | 139517 | Dominguez G, 2003 | |
| PCDH17 | 143678 | Costa VL, 2011 | |
| PDLIM4/RIL | 225193 | Vanaja DK, 2009 | |
| PENK | 192372 | Ueki, 2001 | |
| PGR | 136065 | Lapidus RG, 1996 | |
| PITX2 | 2224759 | Maier S, 2007 | |
| PLAU/uPA | 140078 | Chen CM, 2003 | |
| PRDM2/RIZ1 | 199507 | Du Y, 2001 | |
| PTEN/MMAC1 | 715625 | Whang YE, 1998 | |
| PTGS2/COX2 | 161544 | Müller HM, 2003 | |
| PXMP4/PMP24 | 2724175 | | |
| PYCARD/ASC/TMS1 | 714253 | Akahira J, 2004 | |
| RARB | 2723808 | Bovenzi V, 1999 | |
| RARB2 | 2723808 | Sirchia SM, 2000 | |
| RARRE Sl/TIG1 | 149144 | Youssef EM, 2004 | |
| RASSF1 | 691429 | Rabiau N, 2009 | |
| RASSF1A | 259278 | Maruyama R, 2001 | |
| RASSF2 | 2138398 | Akino, 2005 | Blood, Stool |
| RB1 | 221090 | Zemliakova VV, 2003 | |
| RBP1/CRBP1 | 1203838 | | |
| RGS2 | 140287 | Wolff DW, 2011 | |
| RPIA | 684423 | Kim JH, 2011 | |
| RPRM/Reprimo | 142879 | Takashi T, 2005 | |
| RUNX3 | 157489 | Kang GH, 2003 | |
| S100A6 | 173957 | Rehman I, 2004 | |
| SCGB3A1/HIN1 | 138934 | Krop IE, 2001 | |
| SERPINB5/maspin | 138239 | Domann FE, 2000 | |
| SFN/14-3-3 sigma | 914465 | Ferguson AT, 2000 | |
| SFRP1/SARP2 | 164788 | Caldwell, 2004 | |
| SFRP2 | 696181 | Muller, 2004 | Tissue, stool, blood |
| SFRP4 | 2727487 | Qi J, 2006 | |
| SFRP5 | 175342 | Qi J, 2006 | |
| SLC18A2 | 2066003 | Sorensen KD, 2009 | |
| SLC5A8 | 239573 | Li H, 2003 | |
| SLIT2 | 135714 | Dallol A, 2002 | |
| SOCS1 | 137969 | Müller HM, 2003 | |
| SOX11 | 228323 | Chung W, 2011 | |
| SOX17 | 142327 | Zhang W, 2008 | |
| SPARC | 144119 | Sato N, 2006 | |
| SPOCK2 | 913756 | Chung W, 2008 | |
| SPRY4 | 187066 | Wang J, 2006 | |
| STK11/LKB1 | 905752 | Estellar M, 2000 | |
| SVIL | 714368 | Vanaja DK, 2006 | |
| SYK | 199436 | Yuan Y, 2001 | |
| TCF21 | 140186 | Costa VL, 2011 | |
| TERT | 707362 | Müller HM, 2003 | |
| TFAP2E | 1783333 | Douglas DB, 2004 | |
| TFPI2 | 233268 | Glockner, 2009 | Blood |
| TGFB2 | 149923 | | |
| THBS1 | 156773 | Tobias ES, 2001 | |
| TIMP3 | 2360416 | Bachman KE, 1999 | |
| TMEFF2/HPP1/TPEF | 151509 | Tan AC, 2009 | |
| TNFRSF10C/DcR1 | 2725119 | Shivapurkar, 2004 | |
| TNFRSF10D/DcR2 | 164798 | Shivapurkar, 2004 | |
| TNFRSF25/DR3 | 677688 | Friedrich MG, 2004 | |
| TWIST1 | 139222 | Fackler MJ, 2003 | |
| UCHL1/PGP9.5 | 909478 | Okochi-Takada, 2006 | |
| VIM | 624456 | Itkowitz, 2007 | |
| WIF1 | 176983 | Taniguchi H, 2005 | |
| WWOX | 676612 | Kuroki, 2004 | |
| XAF1 | 237012 | Jang JY, 2005 | |
| ZNF132 | 154645 | Abildgaard MO, 2011 | |

TABLE XIII

Methylated biomarkers for Inherited Genetic Disorders or other Diseases or Disorders Associated with DNA Methylation

| Disorder | Genes | UniGene UGIDs |
|---|---|---|
| Beckwith-Wiedemann syndrome/Silver-Russell syndrome | IGF2 | 173422 |
| Beckwith-Wiedemann syndrome/Silver-Russell syndrome | H19 | 1292941 |
| Beckwith-Wiedemann syndrome/Silver-Russell syndrome | KCNQ1 | 141722 |
| Beckwith-Wiedemann syndrome/Silver-Russell syndrome | p57 Kip2/CDKN1C | 143634 |
| Cancers | H19 | 1292941 |
| Cancers | IGF2R | 702221 |
| Cancers | MLH1 | 161374 |
| Cancers | PEG1/MEST | 173141 |
| Cancers | Gamma2-COP | 131863 |
| Cancers | GRB10 | 1780808 |
| Prader-Willi syndrome/Angelman's syndrome | SNRPN/SNURF | 1780341 |
| Prader-Willi syndrome/Angelman's syndrome | UBE3A | 2067873 |

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of verifying proper function of a test for detecting, monitoring or classifying a disease or disorder, or a predisposition thereto, for which manifestation of a methylated gene or other methylated DNA sequence is a biomarker, comprising:
forming a control that originates from at least one pregnant female animal, wherein forming the control further comprises:
obtaining blood from a plurality of pregnant female animals,
pooling the blood from the plurality of pregnant female animals,
isolating a plasma fraction from the pooled blood of the plurality of pregnant female animals,
extracting DNA from the plasma fraction, and
treating the DNA with a reagent or a group of reagents that provides for determination of methylation status of said biomarker;
obtaining at least one biological sample from an animal subject;
performing the test, wherein the test includes determining the methylation status of at least one biomarker from a biological sample obtained from the animal subject; and
verifying proper function of the test by determining the methylation status for the control, wherein a positive methylation status observed in the control indicates that the test functioned properly.

2. The method of claim 1, wherein the disease or disorder tested for is a solid cancer, hematologic cancer, or other malignancy.

3. The method of claim 1, wherein the predisposition to a disease or disorder is a predisposition to a genetic syndrome or disease.

4. The method of claim 1, wherein the biological sample is selected from the group consisting of: cell lines, histological slides, biopsies, paraffin-embedded tissue, body fluids, stool, colonic effluent, urine, saliva, blood plasma, blood serum, whole blood, isolated blood cells, cells isolated from the blood, and combinations thereof.

5. The method of claim 1, wherein the control is blood or methylated circulating nucleic acid originating from the at least one pregnant female animal.

6. The method of claim 1, wherein the at least one pregnant female animal is a mammal.

7. The method of claim 6, wherein the mammal is a human.

8. The method of claim 1, wherein the predisposition to a disease or disorder is a predisposition for cancer.

9. The method of claim 1, wherein the predisposition to a disease or disorders is a predisposition for an inherited genetic syndrome.

10. The method of claim 1, wherein the methylated gene is selected from the group consisting of: ABCC6; CA10; DBC2; HEPACAM; HOXB2; HPSE/HPR1; KRT13; MYO3A; NKX6-2; PMF1; POU4F2; SYNPO2/myopodin; ZNF154; 3OST3B; ACADL; ATOH1/hATH; BECN1; C14; CBFA2T3; COL7A1; CREBBP; CXCL1; EDN3; ERBB4/HER4; ETS1; FAM110A/c20; FAM19A4/FLJ25161; FAT4; FGFR4; FOXC1; FOXF1; GHSR; GJB2/CX26; GPR180/ITR; HDAC1; HSD17B1; HSD17B2; HSD17B4; IPF1; ISL1; ITIH5; LEBREL1/P3H2; LEBREL2/P3H3; LRRC49; MGA; miR-124; miR-196a-2; miR-335; MYBL2; NFIX; NRN1; OGG1; PCDHGB6; PPP2R2B; PRDM12; PTRF; RNF20; ST18; STK36; STMN1; SULT1A1; SYNM; THAP10; TOX; TSC1; UAP1L1; UGT3A1; ZBTB8A; ZNF432; ADAMTS12; ADAMTS5; ADHFE1; BARX1; BEND4; CASR; CD109; CDX1; CNR1/CB(1) receptor; CNRIP1; CNTFR; DEXI; DUSP26; EDIL3; ELMO1; EXTL3; EYA2; FLT1; GJC1; GLP1R; GPR101; GRIN2/NMDAR2A; GSPT2; HOMER2; INA; KCNK12; LAMA1; LRP2/megalin; MBD4/MED1; MCC; miR-342; miR-345; NDRG4; NGFR; NR3C1/GR; PIK3CG; PPARG; PTGIS; PTPRR; QKI; RGMA; SEPT9; SPG20; STARD8; STOX2; TBX5; THBS4/TSP4; TMEM8B/NGX6; VSX2/HOX10; ANGTL2; AXIN; CCBE; CTGF/IGFBP8; DNAJC15; FBXO32; FILIP1L; FZD4; GPR150; GUCY2C; HOXB5; ITGA8; LRP5; miR-130b; NFATX; PTPRN; RUNX1T1; TERC/hTR; TES; TMCO5; IFFO1; ALK; CHGA; CSMD2; DES; DUSP6; ELOVL4; FANCG; FGF2; FGF3; FGF5; FGF8; FGFR1; FLT3; FLT4; GAS1; GEMIN2/SIP1; HIC2; HSD17B12; IGFBP5; ITPR2; LMO1/RBTN1; I-mfa; miR-132; NEFL; NKX2-8; NTRK3/TRKC; NTSR1; PRG2; PTCH2; SLC32A1; TRH; TUBB3; ZNF415; CLSTN1; HIST1H4K; HIST2H2BF; INHA/inhibin alpha; KCNMA1; NKX3.1; NPBWR1/GPR7; NSMCE1/NSE1; PXMP4/PMP24; RGS2; S100A6; SLC18A2; SPRY4; SVIL; TFAP2E; TGFB2; ZNF132; ADAM23; ALDH1A3; APC; BNC1; BRCA1; CADM1/TSLC1/IGSF4; CASB; CAV1; CCNA1; CCND2; CD2/SRBC; CD44; CDH1/E-cadherin; CDH13/H-cadherin; CDKN1C/KIP2/p57; CDKN2A/ARF/p14; CDKN2B/INK4B/p15; CHFR; CIDEA; CLSTN1; COL1A2; CYP1A1; DAB2IP; DAPK1; DBC1; DIRAS(3)/ARHI; DKK3; DLC1; DLEC1; DPYS; EOMES; EPHA5; ESR1/ER-alpha; ESR2/ER-beta; FHIT; FHL1; GAS7; GATA5; GSTP1; HIC1; HIST1H4K; HIST2H2Bf;

HOXA11; HOXA9; HS3ST2/30ST2; ID4; IGF2; IGFBP3; KCNMA1; LAMA3; LAMC2; MAL; MARVELD1; MDFI; MGMT; MINT1/APBA1; MINT2/APBA2; MINT31; miR-34a; miR-34b; miR-34c; miR-9-1; MLH1; MMP2; MSH2; MSX1; MYOD1/MYF-3; NID2; NKX3-1; NPBWR1; NSMCE1/NSE1; OPCML; p14; PCDH17; PDLIM4/RIL; PENK; PGR; PITX2; PLAU/uPA; PRDM2/RIZ1; PTEN/MMAC1; PTGS2/COX2; PXMP4/PMP24; PYCARD/ASC/TMS1; RARB; RARB2; RARRES1/TIG1; RASSF1; RASSF1A; RASSF2; RB1; RBP1/CRBP1; RGS2; RPIA; RPRM/Reprimo; RUNX3; S100A6; SCGB3A1/HIN1; SERPINB5/maspin; SFN/14-3-3 sigma; SFRP1/SARP2; SFRP2; SFRP4; SFRP5; SLC18A2; SLC5A8; SLIT2; SOCS1; SOX11; SOX17; SPARC; SPOCK2; SPRY4; STK11/LKB1; SVIL; SYK; TCF21; TERT; TFAP2E; TFPI2; TGFB2; THBS1; TIMP3; TMEFF2/HPP1/TPEF; TNFRSF10C/DcR1; TNFRSF10D/DcR2; TNFRSF25/DR3; TWIST1; UCHL1/PGP9.5; VIM; WIF1; WWOX; XAF1; ZNF132; IGF2; KCNQ1; H19; IGF2R; p57 Kip2/Art CDKN1C; PEG1/MEST; Gamma2-COP; GRB10; SNRPN; SNURF; UBE3A and combinations thereof.

* * * * *

```
                          SEQUENCE LISTING

<160> NUMBER OF SEQ ID NOS: 14

<210> SEQ ID NO 1
<211> LENGTH: 19
<212> TYPE: DNA
<213> ORGANISM: artificial sequence
<220> FEATURE:
<223> OTHER INFORMATION: completely synthesized

<400> SEQUENCE: 1
aaataatccc atccaacta                                              19

<210> SEQ ID NO 2
<211> LENGTH: 25
<212> TYPE: DNA
<213> ORGANISM: artificial sequence
<220> FEATURE:
<223> OTHER INFORMATION: completely synthesized

<400> SEQUENCE: 2
gattgttgtt tattagttat tatgt                                       25

<210> SEQ ID NO 3
<211> LENGTH: 33
<212> TYPE: DNA
<213> ORGANISM: artificial sequence
<220> FEATURE:
<223> OTHER INFORMATION: completely synthesized

<400> SEQUENCE: 3
gttattatgt tggattttgt ggttaatgtg tag                              33

<210> SEQ ID NO 4
<211> LENGTH: 18
<212> TYPE: DNA
<213> ORGANISM: artificial sequence
<220> FEATURE:
<223> OTHER INFORMATION: completely synthesized

<400> SEQUENCE: 4
ttaaccgcga aatccgac                                               18

<210> SEQ ID NO 5
<211> LENGTH: 24
<212> TYPE: DNA
<213> ORGANISM: artificial sequence
<220> FEATURE:
<223> OTHER INFORMATION: completely synthesized

<400> SEQUENCE: 5
gtgatggagg aggtttagta agtt                                        24

<210> SEQ ID NO 6
<211> LENGTH: 25
<212> TYPE: DNA
<213> ORGANISM: artificial sequence
<220> FEATURE:
<223> OTHER INFORMATION: completely synthesized

<400> SEQUENCE: 6
ccaataaaac ctactcctcc cttaa                                       25
```

<210> SEQ ID NO 7
<211> LENGTH: 30
<212> TYPE: DNA
<213> ORGANISM: artificial sequence
<220> FEATURE:
<223> OTHER INFORMATION: completely synthesized

<400> SEQUENCE: 7
accaccaccc aacacacaat aacaaacaca                                    30

<210> SEQ ID NO 8
<211> LENGTH: 23
<212> TYPE: DNA
<213> ORGANISM: artificial sequence
<220> FEATURE:
<223> OTHER INFORMATION: completely synthesized

<400> SEQUENCE: 8
tcgaataacg gatttatggt tgc                                           23

<210> SEQ ID NO 9
<211> LENGTH: 23
<212> TYPE: DNA
<213> ORGANISM: artificial sequence
<220> FEATURE:
<223> OTHER INFORMATION: completely synthesized

<400> SEQUENCE: 9
gccgcattaa ctcttctaac tcg                                           23

<210> SEQ ID NO 10
<211> LENGTH: 31
<212> TYPE: DNA
<213> ORGANISM: artificial sequence
<220> FEATURE:
<223> OTHER INFORMATION: completely synthesized

<400> SEQUENCE: 10
ccctactcct acaccgatct acatctccca a                                  31

<210> SEQ ID NO 11
<211> LENGTH: 44
<212> TYPE: DNA
<213> ORGANISM: artificial sequence
<220> FEATURE:
<223> OTHER INFORMATION: completely synthesized

<400> SEQUENCE: 11
acattaactc ttctaactca ccttccatcc ctactcctac acca                    44

<210> SEQ ID NO 12
<211> LENGTH: 24
<212> TYPE: DNA
<213> ORGANISM: artificial sequence
<220> FEATURE:
<223> OTHER INFORMATION: completely synthesized

<400> SEQUENCE: 12
gtgatggagg aggtttagta agtt                                          24

<210> SEQ ID NO 13
<211> LENGTH: 25
<212> TYPE: DNA
<213> ORGANISM: artificial sequence
<220> FEATURE:

-continued

```
<223> OTHER INFORMATION: completely synthesized

<400> SEQUENCE: 13
ccaataaaac ctactcctcc cttaa                                          25

<210> SEQ ID NO 14
<211> LENGTH: 30
<212> TYPE: DNA
<213> ORGANISM: artificial sequence
<220> FEATURE:
<223> OTHER INFORMATION: completely synthesized

<400> SEQUENCE: 14
accaccaccc aacacacaat aacaaacaca                                     30
```